(12) United States Patent
Jankowiak et al.

(10) Patent No.: US 6,541,778 B1
(45) Date of Patent: Apr. 1, 2003

(54) METHOD AND APPARATUS FOR CERAMIC ANALYSIS

(75) Inventors: Ryszard J. Jankowiak, Ames, IA (US); Chris Schilling, Ames, IA (US); Gerald J. Small, Ames, IA (US); Piotr Tomasik, Cracow (PL)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/556,008

(22) Filed: Apr. 20, 2000

Related U.S. Application Data
(60) Provisional application No. 60/130,870, filed on Apr. 23, 1999.

(51) Int. Cl.[7] .............................................. G01N 21/64
(52) U.S. Cl. .................................................. 250/461.1
(58) Field of Search ........................... 250/461.1, 458.1, 250/459.1

(56) References Cited

U.S. PATENT DOCUMENTS

| | | | | |
|---|---|---|---|---|
| 4,406,844 A | * | 9/1983 | Froot | 264/21 |
| 4,679,938 A | * | 7/1987 | Flamholz | 250/458.1 |
| 5,127,730 A | * | 7/1992 | Brelje et al. | 250/458.1 |
| 5,332,905 A | * | 7/1994 | Brooker et al. | 250/458.1 |
| 5,672,816 A | * | 9/1997 | Park et al. | 250/306 |

OTHER PUBLICATIONS

T. Abraham, "Advanced Ceramic Powder and Nano–Sized Ceramic Powder: An Industry and Market Overview," in *Ceramic Transactions vol. 62, Science, Technology, and Commericialization of Powder Synthesis and Shape Forming Processes*, edited by J. J. Kingsley, C. H. Schilling, and J. H. Adair (American Ceramic Society, Westerville, Ohio, U.S.A., 1996), pp. 3–13.

F. F. Lange, "Powder Processing Science and Technology for Increased Reliability," *J. Am. Ceram. Soc.* 72 [1] 3–15 (1989).

F. F. Lange, "Sinterability of Agglomerated Powders," *J. Am. Ceram. Soc.* 67 [2] 83–89 (1984).

C. H. Schilling and J. N. Gray, "Needs and Opportunities for NDE in Ceramic Processing," in *Ceramic Transactions, vol. 67: Nondestructive Evaluation of Ceramics*, C. H. Schilling and J. N. Gray, editors, American Ceramic Society, Westerville, Ohio, 1998, pp. 1–19.

C. H. Schilling, V. J. Garcia, R. M. Smith, and R. A. Roberts, "Ultrasonic and Mechanical Behavior of Green and Partially Sintered Alumina: Effects of Slurry Consolidation Chemistry," *J. Am. Ceram. Soc.* 81 [10] 2629–2639 (1998).

(List continued on next page.)

*Primary Examiner*—Constantine Hannaher
*Assistant Examiner*—Shun Lee
(74) *Attorney, Agent, or Firm*—Dickstein Shapiro Morin & Oshinsky LLP

(57) ABSTRACT

The present invention relates to a method and apparatus for ceramic analysis, in particular, a method for analyzing density, density gradients and/or microcracks, including an apparatus with optical instrumentation for analysis of density, density gradients and/or microcracks in ceramics. The method provides analyzing density of a ceramic comprising exciting a component on a surface/subsurface of the ceramic by exposing the material to excitation energy. The method may further include the step of obtaining a measurement of an emitted energy from the component. The method may additionally include comparing the measurement of the emitted energy from the component with a predetermined reference measurement so as to obtain a density for said ceramic.

16 Claims, 12 Drawing Sheets

OTHER PUBLICATIONS

V. J. Garcia, C. H. Schilling, S. P. Huss, J. N. Gray, M. Sikora, P. Tomasik, and C. P. Li, "X–Ray NDE of Density Gradients During Alumina Powder Consolidation: Effects of Suspension Chemistry," in *Advances in Process Measurements for the Ceramic Industry*, edited by A. JillavenKatesa and G. Y. Onoda (American Ceramic Society, Westerville, Ohio, 1999), pp. 307–322.

R. A. Roberts, "A Dry–Contact Coupling Technique for Ultrasonic Nondestructive Evaluation of Green–State Ceramics", *Mater. Eval.* 46 [May] 758–66, (1988).

D. Segal, "Processing of Ceramics Part I" Materials Science and Technology A Comprehensive Treatment, vol. 17A (ed. by R. J. Brook, R. W. Cahn, P. Haasen, E. J. Kramer). pp. 71–98.

\* cited by examiner

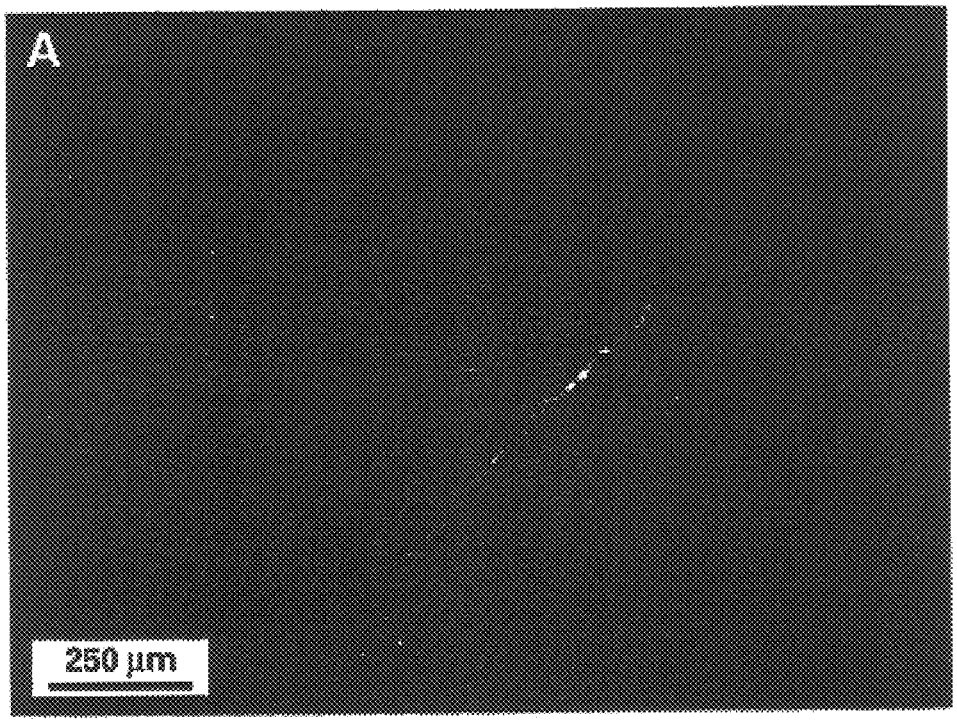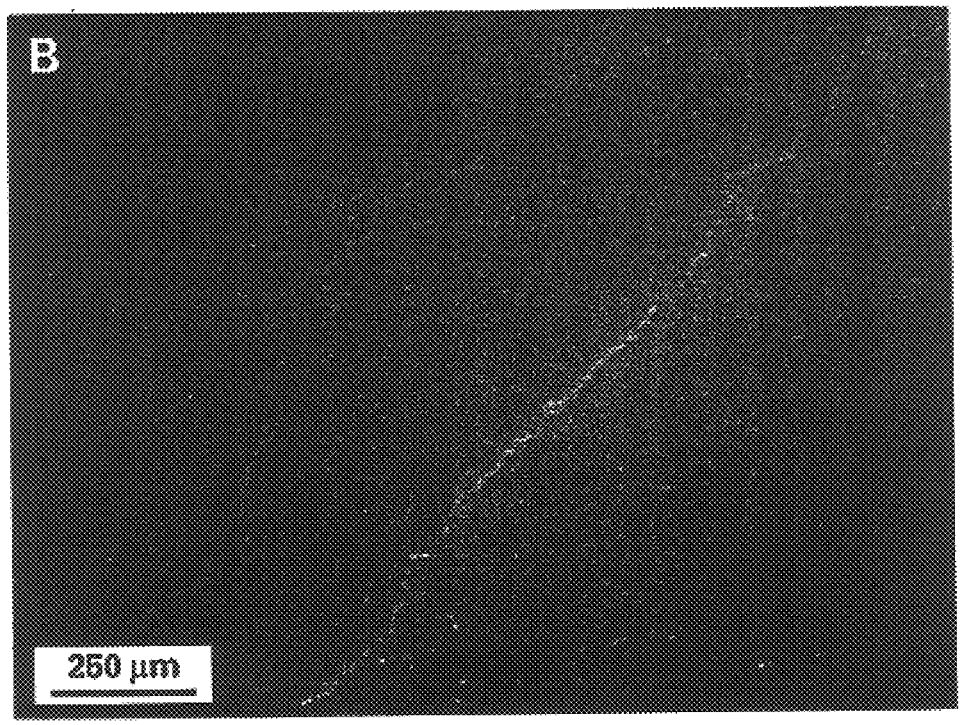
Fig. 5

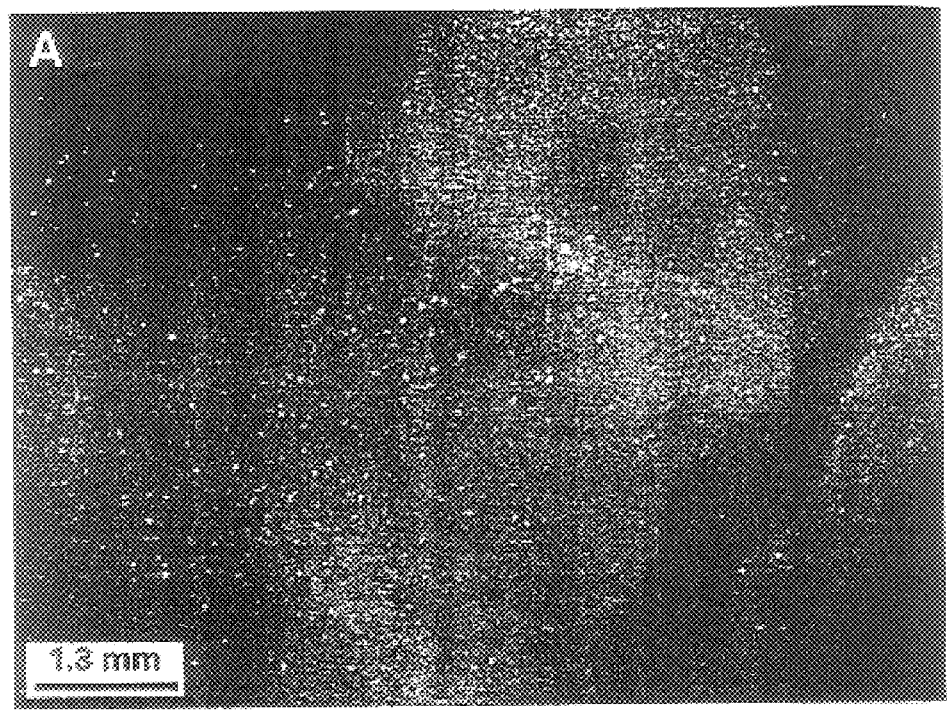
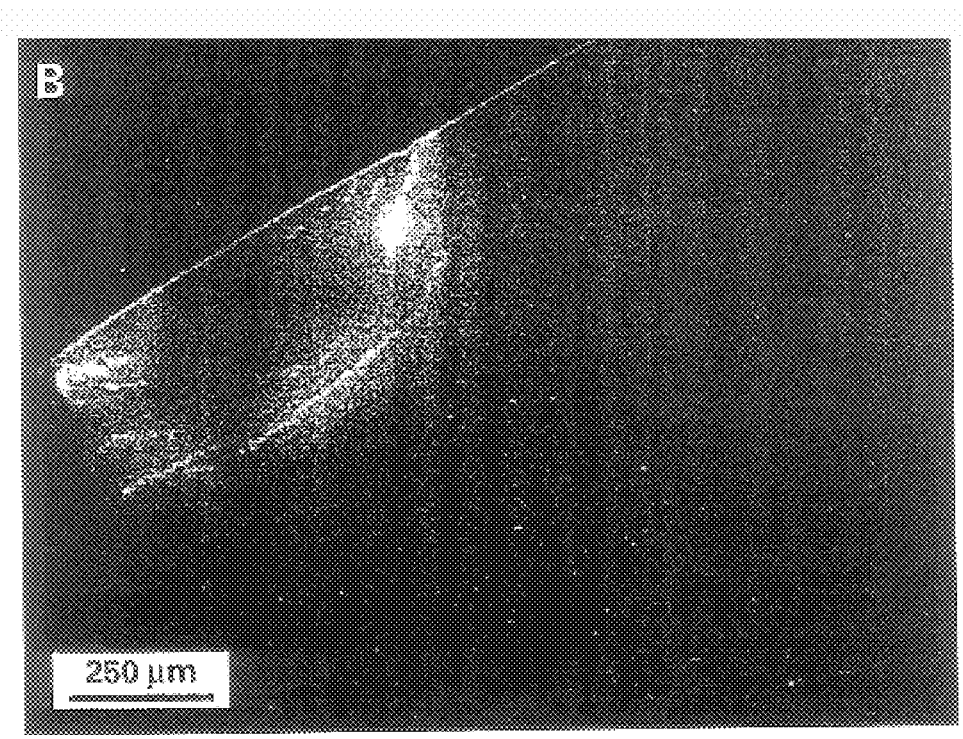
Fig. 6

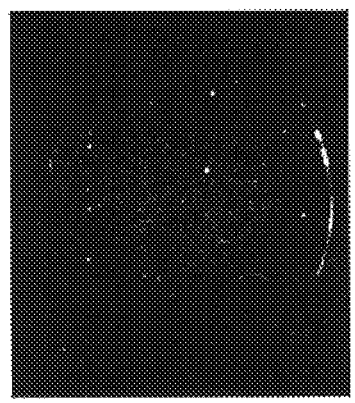
62 vol.%
"green body"
A
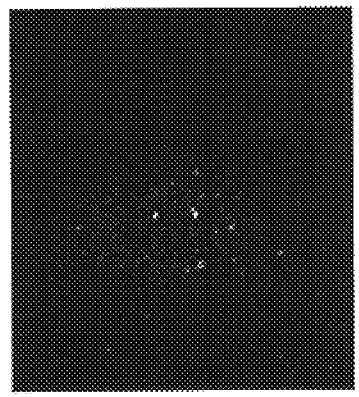
71 vol.%
sintered at 1200°C
B
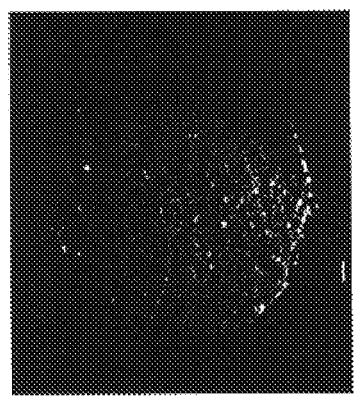
77 vol.%
sintered at 1300°C
C
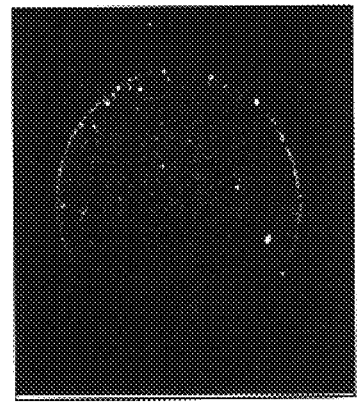
97 vol.%
sintered at 1500°C
D
Fig. 12

METHOD AND APPARATUS FOR CERAMIC ANALYSIS

This application claims priority from United States provisional application Ser. No. 60/130,870, filed Apr. 23, 1999.

The United States Government has certain rights in this invention pursuant to Contract Number W-7405-ENG-82 between the Department of Energy and Iowa State University.

REFERENCES

Several publications are referenced herein by Arabic numerals within parenthesis. Citations for these references may be found at the end of the written description of the present invention. The disclosures of these publications are hereby incorporated herein by reference in their entirety, unless otherwise noted.

BACKGROUND OF THE INVENTION

Ceramic materials are currently widely used in advanced engineering applications, including insulating microelectronic substrates and forming structures such as metallurgical crucibles, liquid metal filters, components (e.g., nozzles, pump valves, seals, etc.) for handling highly corrosive liquids, and medical devices, to name a few. Currently, alumina is the most prevalent ceramic material used in advanced engineering applications, including dielectric substrates, biomedical devices, automotive parts, and other structures and components (1–3). Like most ceramics, the mechanical properties of sintered alumina are greatly compromised by microstructural heterogeneities introduced during shape forming by powder compaction, slip casting, injection molding, and other methods. Common heterogeneities are porosity gradients, isolated pores, cracks, and agglomerates (4–5).

Ceramic materials are typically produced using a sequential process of mixing ceramic powder with an organic liquid carrier (e.g., alcohols, ketones, polyethylene wax, and vinyl compounds) to form a moldable slurry, forming the slurry into a desired configuration (e.g., by injection molding or plastic shaping), thermally treating to evaporate or pyrolyze the carrier, and kiln firing. During the process, microstructure heterogeneities can be introduced during any one or more of these steps, for example, synthesizing of the powder, evaporating the carrier, and kiln firing. Such heterogeneities can include porosity gradients, impurities, isolated pores, cracks, agglomerates, and more significantly, nonuniform -green density that can produce nonuniform shrinkage stresses during drying. Such nonuniform green density can lead to cracks and/or shape distortion of the kiln-fired (sintered) ceramic product.

Traditional methods of quality control, including pycnometry, mechanical property measurements, fractography, and mercury porosimetry, are difficult to use when attempting to optimize the many different processing variables that ordinarily affect microstructure-defect evolution in ceramic production (6). The conventional apparatuses and techniques usually involve slow and costly trial-and-error procedures that are destructive and typically require significant alteration of the ceramic piece for analysis. For example, conventional techniques typically require cutting a ceramic piece for analysis into many small pieces and then performing microscopy, density measurements (by Archimedes immersion principle) and the like, on every piece. This is a potentially significant problem in green body analysis, due to the fragile nature of green bodies that often require application of preservation techniques to the green body before analysis. Such preservation techniques include, but are not limited to, chemical fixation or drying, followed by partial sintering, cutting, and polishing. Consequently, there is an increased potential for the introduction of contaminants through the preservation process.

Researchers are currently attempting to use ultrasound and x-rays to map density gradients in ceramics (6–8), but there are problems adapting these methods to production environments. For example, x-ray methods are not always fast enough or affordable in a production setting. A concern with ultrasound is that it requires liquid coupling media, which often disintegrates green bodies. "Air-coupled" ultrasound was recently developed to overcome the problem of disintegration, but this technology has not been fully developed for ceramic production (9–10).

Thus, what is yet needed is a method and apparatus for analyzing ceramics. In particular, what is needed is a method and apparatus for analysis of a ceramic, such as for the analysis of the density, density gradients and/or microcracks in a given ceramic sample, which can be accomplished relatively quickly, easily, without destruction of the ceramic sample during evaluation, and preferably at a lower cost than conventional methods for detecting density and/or microcracks.

SUMMARY OF THE INVENTION

One aspect of the present invention provides an apparatus for analyzing ceramic density gradients and/or microcracks, including an excitation source capable of exciting a component in a ceramic surface; a charge-couple device; and a processor, operably linked to the charge-couple device, wherein the processor is at least capable of integrating a luminescence intensity generated by exciting the component. Preferably, the excitation source comprises a laser capable of emitting energy having an associated wavelength within an ultraviolet spectrum or an infrared spectrum. More preferably, the excitation source is capable of exciting an impurity ion (e.g., $Cr^{+3}$) that in turn luminesces.

Another aspect of the present invention provides an apparatus for analyzing microcracks, including an excitation source capable of exciting a component in a ceramic surface; a detector operably linked to the excitation source; a translation portion capable of adjusting a position of a ceramic in at least one direction relative to the excitation source; and processor operably linked to the detector, wherein the processor is at least capable of comparing a measurement obtained from exciting the component to a predetermined background measurement. Preferably, the excitation source comprises a laser capable of emitting energy having an associated wavelength within an ultraviolet spectrum or an infrared spectrum. Preferably, the excitation source is capable of exciting a chromium ion.

A further aspect of the present invention provides a method for analyzing density of a ceramic comprising exciting a component on a surface of the ceramic by exposing the surface to energy. The method further includes the step of obtaining a measurement of an emitted energy from the component. The method additionally includes comparing the measurement of the emitted energy from the component with a predetermined reference measurement so as to obtain a density for said ceramic.

Another aspect of the present invention provides a method for analyzing a density gradient and/or microcracks of a ceramic comprising exciting a component on a surface of the ceramic. The method further includes obtaining a measurement of an emitted energy from the component. Additionally, the method includes imaging the ceramic so as to visually indicate a density gradient and/or microcracks associated with the measurement.

Another aspect of the present invention provides a method for analyzing a density gradient and/or microcracks of a ceramic comprising scanning in at least one direction of a surface of said ceramic with an input energy so as to excite components from the surface of the ceramic. Additionally, the method includes obtaining a measurement of an emitted energy from the components and observing the measurement of the emitted energy so as to indicate density gradients and/or microcracks associated with the measurement.

Yet another aspect of the present invention provides a method for analyzing a density gradient and/or microcracks of a ceramic comprising chemically reacting a ceramic with a chemically reactive solution so as to cause emission of energy from components in the ceramic. Additionally, the method includes observing the emitted energy so as to indicate density gradients and/or microcracks associated with the emitted energy.

In the methods described above, the ceramic can be a sintered ceramic or a green ceramic. In a preferred embodiment, the ceramic comprises alumina, wherein the component comprises a chromium ion.

In another aspect of the invention there is provided a chemiluminescent kit comprising one or more chemiluminescent materials which synergistically impart enhanced luminescence to ceramics.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 shows fluorescence images of a sintered alumina specimen.

FIG. 6 shows fluorescence images of a sintered alumina.

FIG. 12 shows the color dependence on sample density of an alumina ceramic.

DETAILED DESCRIPTION OF THE PREFERRED EMBODIMENTS

The apparatus and method for analyzing ceramics, in particular for detecting, e.g., density, density gradients and/or microcracks, of a preferred aspect of the present invention is as follows. As used herein, "ceramic(s)" refers to a material including a metallic component and a nonmetallic component. Ceramics include, but are not limited to, porcelain, refractories, glass, nonmetallic magnetic materials, ferroelectrics, metal oxides, manufactured single crystals, and any combination thereof. Components typically included in ceramics are oxygen, silicon, aluminum, iron, calcium, sodium, potassium, magnesium, hydrogen, nitrogen, phosphorus, carbon and combinations thereof, as well as others which may be known in the art. Specific examples of a ceramic include alumina ($Al_2O_3$), zirconia ($ZrO_2$), thoria ($ThO_2$), beryllia (BeO), magnesia (MgO), calcium phosphate ($Ca_3(PO_4)_2$), spinel ($MgAl_2O_4$), forsterite ($Mg_2SiO_4$), electrooptic ceramics (e.g., lithium niobate ($LiNbO_3$) and lanthanum-modified lead zirconate titanate (PLZT)), ceramic nitrides (e.g., aluminum nitrides and silicon nitrides) and silicon carbide (SiC). The foregoing ceramics will also contain additional amounts of metal ions, e.g., transition metal ions, which are often naturally present in the ceramics or which may have been implanted or "doped" using any suitable method. For example, transition metal ions, e.g., chromium ions, are typically found in most ceramics. Thus, alumina which contains chromium ions may be represented by the formula $Al_2O_3{:}Cr^{3+}$, and so on. Metal ions which are present in the ceramic, either naturally or by implantation/doping, are usually present in amounts of less than about 1% by total weight of the ceramic.

Also, as used herein, "green" refers to a mixture of ceramic ingredients that has been dried but not yet densified, typically by sintering (kiln firing). A green body is typically a shaped, dried mixture of ceramic ingredients. Ingredients typically used in making ceramics include sands, clay, fine particulate solids (e.g., $Al_2O_3$, $ZrO_2$, MgO, $Ca_3(PO_4)_2$, etc.), binders (e.g., organic material), lubricants (to reduce friction and aid in release of the body from a mold after shaping), wetting and water retention agents, deflocculants (to control pH, electrostatic charge, and particle dispersion) and sintering aids, to name a few. Further, as used herein, "ceramic surface" refers to either a surface of a sintered ceramic material or a surface of an unsintered, non-kiln fired ceramic material.

Figure 1:
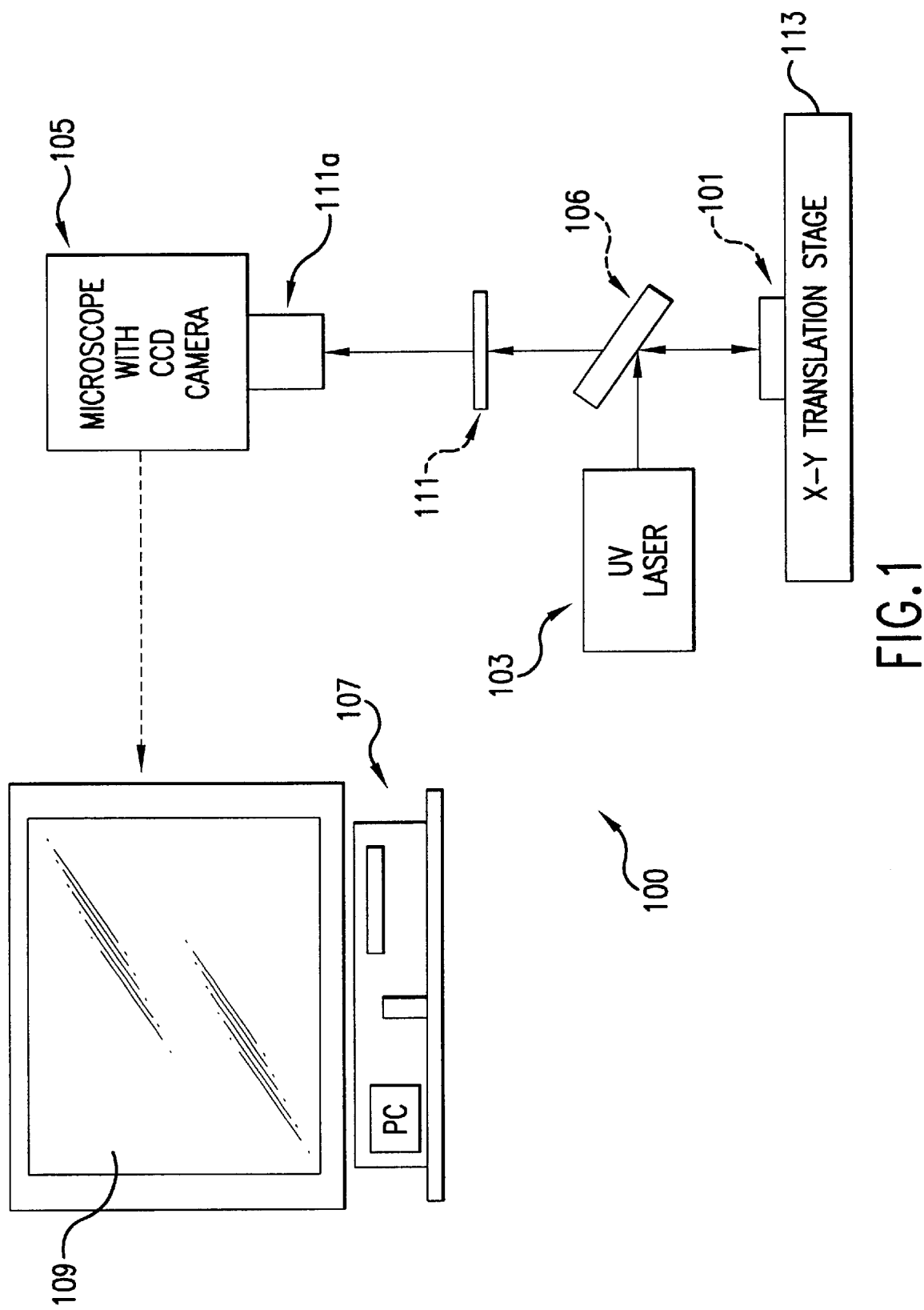
FIG. 1 shows an apparatus for analyzing an alumina specimen according to a preferred embodiment of the present invention.

FIG. 1 provides a preferred apparatus 100 for analyzing surface defects of a ceramic surface that includes an excitation source 103, preferably a pure output laser, i.e., a laser emitting energy of a single wavelength, capable of exciting a component in the ceramic surface 101 and a detector 105 capable of measuring energy emitted from the component once excited by the energy source. Alternatively, the wavelength of the laser can be chosen by a dichroic mirror 106. Preferably, the detector includes a charge-couple device (CCD) to provide 3-D plots and to capture color images. Other suitable imaging systems in addition to or in lieu of a CCD are also contemplated for use herein. A processor 107 can be provided to integrate luminescence intensity of the energy emitted from the component. Once the color images have been captured, they can be stored in the processor 107 or other suitable device, and separated into their color components that can be converted to a grayscale image 109, for example. The grayscale image can be obtained from within a region of interest, e.g., from an area suspected of having defects or cracks, where the total intensity can then be correlated with a sample density plot, hereinafter described. A suppression filter 111 between the dichroic mirror 106 and the detector 105 acts to minimize or eliminate any "leakage" emission or radiation from the excitation source 103.

An objective such as a lens 111a or other focusing device is preferably included so that energy emitted from the ceramic surface passes through the lens 111a prior to entering the detection system as set forth above. In one preferred embodiment, the lens is an uncoated plano-convex lens with a suitable focal length that can be used to focus the energy emitted from the ceramic surface 101 and collect emitting fluorescence which is perpendicular to the excitation source. Useful lenses, such as a 12 mm lens, are available from, for example, Edmund Scientific, Barrington, N.J.

Optionally, a cutoff filter can also be employed to block scattered light depending upon the excitation laser employed. Thus, if a 514 nm laser is utilized, a cutoff filter suitable for 514 nm may be used, such as an RG610 filter available from, for example, Corning Glass, Corning N.Y. Further, the apparatus 100 can include a translation portion 113 such that the ceramic surface 101 can be scanned with the energy source 103 moving in at least one direction, e.g., the "x" direction. In other preferred embodiments, the translation portion 113 may permit scanning in at least two directions, "x" and "y", and even three directions, "x", "y" and "z".

Utilizing such an apparatus, it is now possible to detect defects according to the non-destructive method of the present invention. In one embodiment of the invention, the density of a ceramic can be determined utilizing luminescence spectroscopy. Luminescence is achieved by exciting one or more metal ions, e.g., Cr, Fe, Ti, Ga, B, Zn, Ce, etc., and preferably $Cr^{+3}$, present in the ceramic sample.

Figure 2:
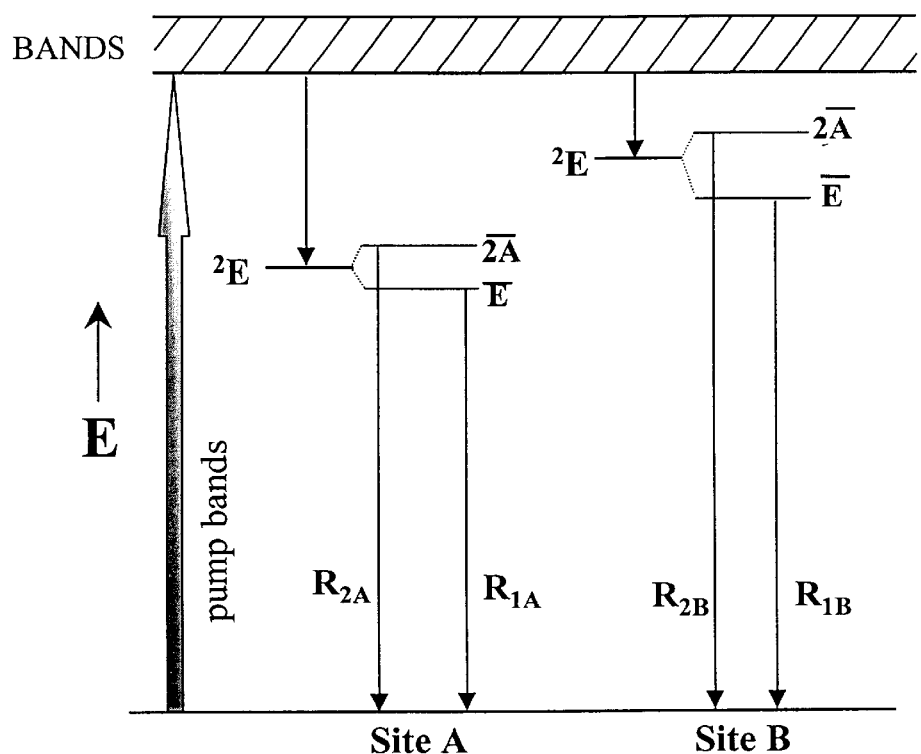
FIG. 2 shows a simplified energy diagram of the experimentally observed transitions for fluorescence of $Cr^{3+}$ metal ions in $\alpha$-alumina.

As an example, FIG. 2 shows a simplified energy diagram of the experimentally observed transitions for fluorescence of $Cr^{3+}$ metal ions in α-alumina. As heretofore described, any suitable source can provide the excitation energy. This source is preferably a laser, and more preferably is an inert gas laser beam, e.g., Ar, He, Xe, etc., and preferably is an Ar-ion laser beam. Further, the laser is preferably either in UV or red spectral mode, preferably utilizing wavelengths in the region of about 300 nm to about 400 nm, more preferably about 350–352 nm or wavelengths in the regions of about 500 nm to about 650 nm, preferably about 513–515 nm, respectively. The excited ions, e.g., $Cr^{+3}$, will typically luminesce within the range of about 650–850 nm, preferably about 650–780 nm. Those skilled in the art will recognize that emitted energy having a wavelength outside the preferred ranges is possible, depending upon the given ion or ions which may be excited. For example, emission in the blue and green spectral regions may also be observed and may originate from other ions.

Figure 3:
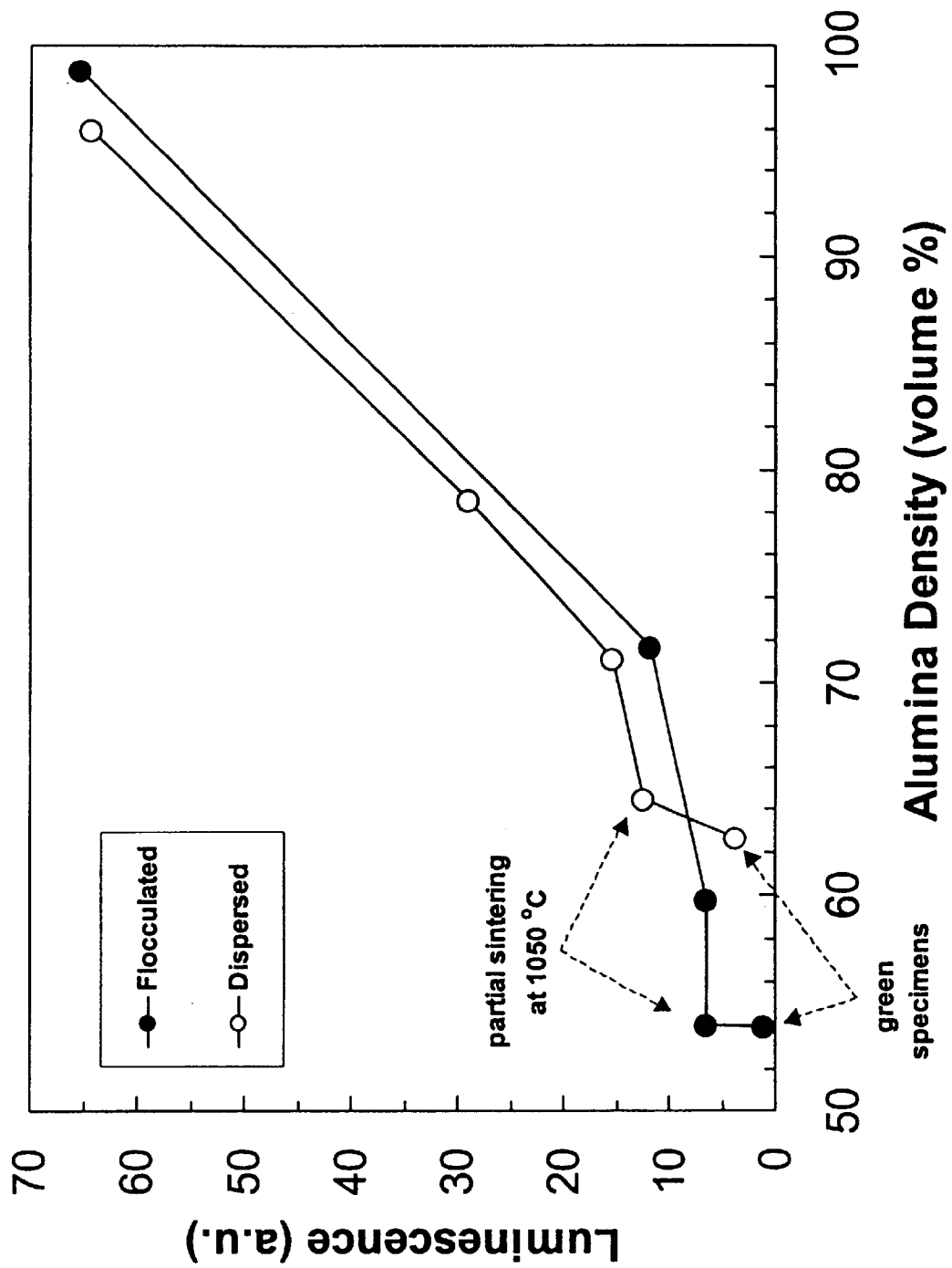
FIG. 3 shows a luminescence—density calibration curve for alumina.

This energy from electron excitation of the metal ions in the form of luminescence of the component in the ceramic surface can then be compared to a predetermined reference measurement of luminescence generated from a reference ceramic having a known density. Hence, a luminescence calibration curve for a given ceramic composition sintered at increasing temperatures can first be calculated and plotted as shown in FIG. 3 (in other embodiments, the plot in FIG. 3 can also represent the compilation of several measurements for a given ceramic composition/density). Thereafter, the luminescence of a "production" ceramic sample can be compared to this plot. In other words, in a production setting, the density of a ceramic sample is determined in a non-destructive fashion by obtaining the luminescence measurement of the ceramic sample and then comparing that luminescence to the calibration curve of FIG. 3 representing various densities as a function of luminescence for a particular input energy. To determine whether the ceramic sample is of a particular, desirable density, the skilled artisan will simply illuminate (or excite) the ceramic sample as heretofore described and determine whether the intensity of the luminescence is that of ceramic with a particular density, by comparing the luminescence for the sample to that of the corresponding reference density measurement on the calibration curve.

Figure 4:
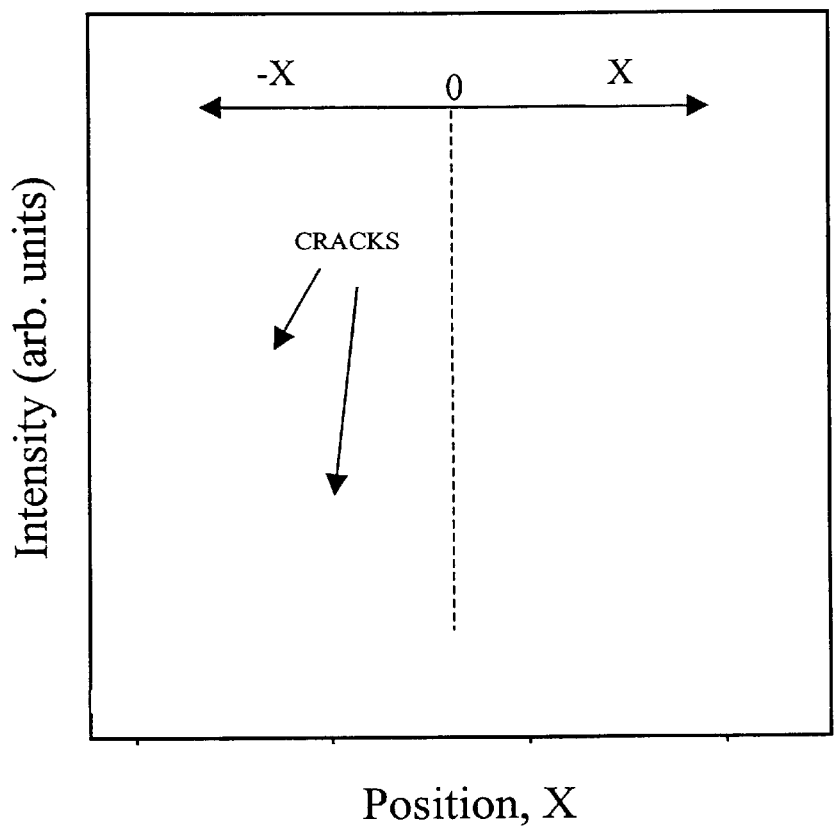
FIG. 4 shows the luminescence intensity as a function of sample position.

In another preferred embodiment of the invention, density gradients and/or cracks in a ceramic are detected by scanning a semi-focused (not fully focused) laser beam across the surface of the ceramic in the manner as represented in FIG. 4. As the laser beam is scanned, trace amounts of metal ions, e.g., Cr, Fe, Ti, Ga, B, Zn, Ce, etc., preferably $Cr^{+3}$, which are present in the ceramic are excited. Once again, the excitation can be caused by an inert gas laser beam, e.g., Ar, He, Xe, etc., preferably an Ar-ion laser. Further, the laser can be either in UV or red spectral mode, preferably utilizing wavelengths in the region of about 300 nm to about 400 nm, preferably about 350–352 nm or wavelengths in the regions of about 500 nm to about 650 nm, preferably about 513–515 nm. A ceramic specimen (e.g., one that is partially sintered) can be scanned, for example, in the forward direction (+X) followed by scanning the same distance in the reverse direction (−X). When the beam encounters a crack or microcrack, an increase in luminescence intensity is observed. Conversely, when the laser beam is scanned on a smooth, substantially defect-free portion of the ceramic sample, background luminescence is observed. However, when an imperfection such as a microcrack is encountered, luminescence increases because of a larger cross section of the ceramic being exposed to the laser light and/or tighter focus of the laser beam within the microcrack. Thus, scanning according to this embodiment is useful in nondestructive evaluation of cracks and/or density gradients in ceramic processing.

In yet another preferred embodiment of the invention, density gradients and/or microcracks are revealed utilizing imaging techniques as shown in FIGS. 5 and 6, with further reference to Examples 5 and 6. Any of the methods heretofore set forth for detecting defects can further comprise the step of applying a composition to the ceramic surface prior to exposing the surface to energy. Preferably, the composition includes a dye or a fluorescent agent, or a combination thereof, that emits visible radiation in passing from a higher to a lower electronic state, typically in which the time interval between adsorption and emission of energy is relatively short, preferably on the order of about $10^{-8}$ to about $10^{-3}$ second. One type of suitable fluorescent compounds are compounds that emit visible radiation when excited by wavelengths in a range selected from the group consisting of the UV range (typically about 300 nm to about 400 nm), the visible and/or red range (typically about 500 nm to about 700 nm), and a combination thereof. Preferred fluorescent compounds include fluorescein, rhodamine, luciferin, and compositions, e.g., FAM, JOE, ROX, TAMRA, Cy3, and Cy5. Other suitable agents include energy transfer coupled dyes including a donor and an acceptor dye. Application of the composition to the ceramic comprises contacting or "staining" at least a portion and preferably the entire surface and more preferably including at least part of the subsurface of the ceramic with the composition. This staining is performed for a period of time sufficient for the ceramic surface to substantially absorb the composition, and will typically be performed for about 2–5-minutes, which time may vary according to the size of the surface and other factors such as the underlying material comprising the ceramic and/or its density/porosity. After the contacting or staining step, it is then preferable to follow the contacting step by removal of any excess, non-absorbed composition from the ceramic surface. This removal step can involve washing the sample thoroughly, e.g., with deionized water or other suitable material, to remove any non-absorbed dye. Thereafter, the ceramic is preferably allowed to dry before subsequent analysis. Preferably, one or more of the following industry-available sets of excitation filters is then be used for fluorescence based imaging of the ceramic surface: a UV filter set; a violet filter set; and a green filter set. Use of two or more of the foregoing filters would involve sequential analysis, e.g., first observation with the UV filter set, followed by observation with the violet filter set, and then observation using the green filter set. Other spectral filters may also be utilized by the skilled artisan. As shown in FIGS. 5 and 6, lower or less dense regions on the ceramic surface which have been contacted with the composition are revealed by the filters to have a greater luminescent intensity. These lower or less dense regions are indicative of cracks or other structural defects in the ceramic.

In a further preferred embodiment of the invention, the color images as heretofore described are processed into grayscale images with contrasting hues of dark and light areas using photomethodology known in the art. In areas where the density is relatively higher than other areas of the ceramic, a greater proportional number of excited metal ions will be observed. This excitation will translate into an image that is darker, or brighter as compared to areas that are not as dense. Thus, in a captured image of a particular sample, whether it be greyscale or color photography, density gradients are easily distinguishable as light and dark regions, and microcracks can be observed as predominant, typically diagonal stretch marks across each image. Imaging according to this embodiment is particularly useful in nondestructive evaluation of density gradients and/or microcracks in ceramic processing.

Figure 7:
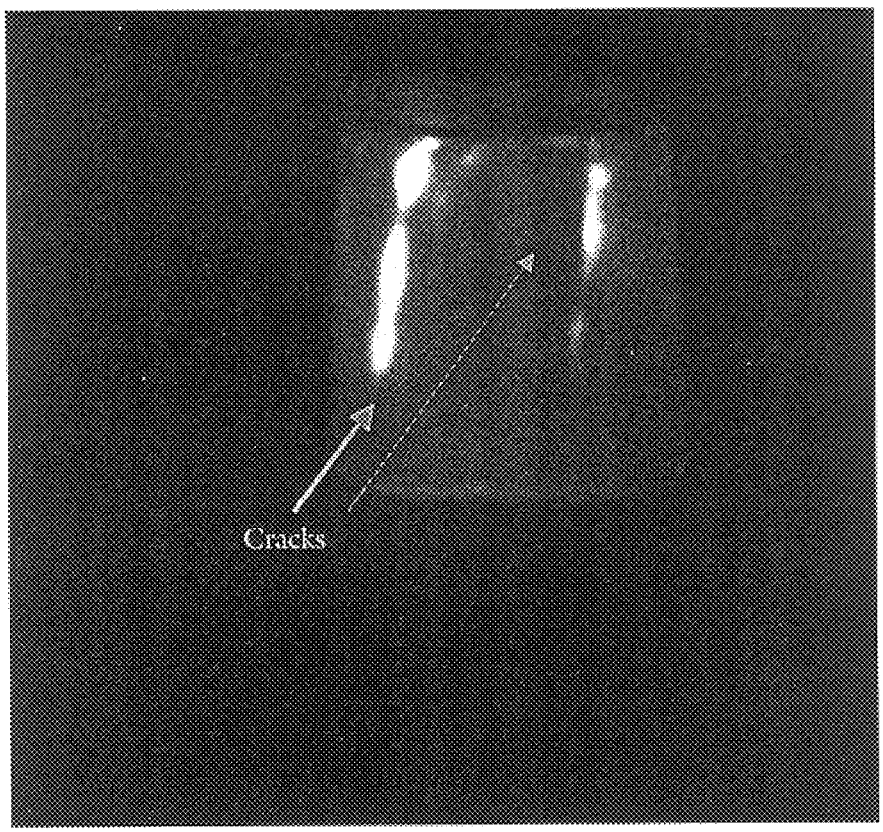
FIG. 7 shows chemiluminescent based images of cracks.
Figure 8:
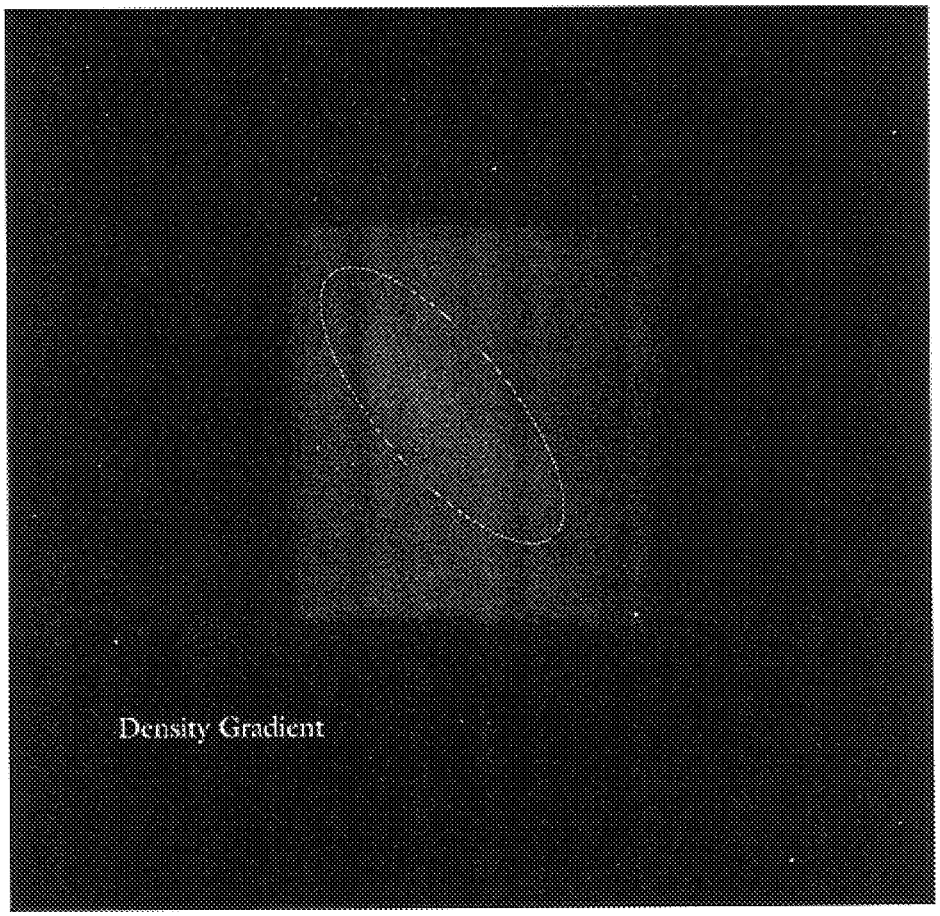
FIG. 8 shows chemiluminescent based images of density gradients.

In another preferred embodiment of the present invention, density gradients and/or microcracks are observed by utilizing chemiluminescence as shown in FIGS. 7 and 8. Chemiluminescence-based imaging provides detection and visualization of imperfections, e.g., cracks and density gradients, in various ceramics, preferably alumina. Moreover, chemiluminescence-based imaging may be accomplished without external excitation, e.g., without a laser. In addition, this method is particularly useful for detecting defects inside the ceramic. According to this embodiment, the ceramic is first contacted with one or more chemiluminescent materials, which may be provided separately or together in kit form. The ceramic is preferably contacted for about 1–2 minutes with one or more of a fluorescent dye, e.g., 9, 10-bis (phenylethynyl) anthraene (BPEA) (Fluka 15246), 9, 10-diphenylanthra-ene (DPA) Fluka 42785, and/or fluorescein; a diphenyl oxalate (such as oxalic acid dephenyl ester); and hydrogen peroxide, and preferably an admixture of all three. In a preferred embodiment of the invention, one or more of the foregoing materials, and desirably all three, are first admixed with a solution of a chemiluminescent initiator material (e.g., a salicylate catalyst, for example, salicylate acid sodium salt ($C_7H_5O_3Na$)) and a sintered ZYGLO® fluorescent (with, for example, methyl diamine-coumarin, and/or Hudson Yellow) penetrant. It has now been discovered that a combination of the foregoing chemiluminescent materials preferably provides about 10 to about 100 times the luminescent intensity of, for example, either a combination of a fluorescent dye, an oxalate and hydrogen peroxide alone, or the combination of a chemiluminescent initiator material and a penetrant/fluorescent dyes alone.

After contacting the ceramic with the foregoing material(s), the excess is then preferably wiped off, dried or otherwise removed. The ceramic will chemiluminesce with one or more of these materials. In areas where the density is relatively higher than other areas of the ceramic, a greater proportional number of excited metal ions will be observed. This excitation translates into a chemiluminescent image that is darker, as compared to areas that are not as dense. Thus, in a captured image of a particular sample, density gradients are easily distinguishable as light and dark regions and microcracks can be observed as a prominent, diagonal marks within each image. Chemiluminescent imaging according to this preferred embodiment is particularly useful in nondestructive evaluation of density gradients and/or microcracks in ceramic processing.

In another preferred embodiment of the invention, luminescent material(s) are admixed with the liquid constituents (e.g., solvents, binders, and plasticizers) during the slurry preparation stage of ceramic manufacture. For example, the chemiluminescent material(s) heretofore described and/or certain phosphorescent molecules, e.g., pyridine, sulfapyridine, sulfamerazine, anthraquinone, etc., can be added to a liquid suspension of ceramic powder prior to spray-drying (or freeze-drying) and green-body formation by dry powder compaction. Another example is to mix these luminescent material(s) into slurries that subsequently undergo shape-forming by various methods including, e.g., slip casting, injection molding, tape casting, laminated object manufacturing, gelcasting, and other suitable methods. In each of these cases, the luminescent material(s) are all preferably retained in the green body throughout shape-forming. The green body thereafter luminesces, e.g., phosphoresces, thereby enabling detection of surface cracks and surface density gradients. Preferably, the luminescent material(s) subsequently evaporate from the green body during, for example, a debinding stage of manufacturing (e.g., heating to approximately 200 to 300° C. to pyrolyze organic materials residing between the ceramic powders in the green body just prior to kiln firing or sintering.)

EXAMPLES

Materials and Methods

Exemplary sources and/or names of some of the materials utilized in the present invention will be indicated where noted. These are, however, only exemplary and are hot meant to limit the scope of the present invention in any way.

Apparatus for Analyzing Ceramic Defects

FIG. 1, as discussed previously, provides an apparatus 100 for analyzing surface defects of a ceramic surface that includes an excitation source 103 capable of exciting a component in the ceramic surface 101 and a detector 105 capable of measuring energy emitted from the component once excited by the energy source. The wavelength of the laser can be chosen by the dichroic mirror 106. The detector 105 includes a charge-couple device (CCD) to provide 3-D plots and to capture color images. A processor 107 is provided to integrate luminescence intensity of the energy emitted from the component. Once the color images have been captured, they are stored in the processor 107, separated into the color components that can be converted to a grayscale image 109. The grayscale image can be obtained from a region of interest, where the total intensity can be correlated to sample density. A filter 111 is included so that energy emitted from the ceramic surface passes through the lens 111a prior to entering the detection system. The objective (111a) is an uncoated plano-convex lens and should have a suitable focal length that can be used to focus the energy emitted from the ceramic surface 101 that can be used to focus and collect emitting fluorescence perpendicular to the excitation source. A cutoff filter can be employed to block scattered light and is dependent upon the excitation laser employed. Further, apparatus 100, includes a translation portion 113 such that the ceramic surface can be scanned with the energy source 103 in at least one direction.

Sample Preparation and Density Measurements of Ceramic Pellets

Slip casting was used to consolidate colloidal suspensions of α-alumina powder into pellets having a controlled range of bulk density. The bulk density was regulated by controlling the sintering temperature and by altering the particle packing structure of the green pellets, which, in turn, was controlled by the degree of interparticle repulsion/attraction in the slip casting suspension. For comparative purposes, luminescence measurements were conducted on fully-dense, commercially-available specimens of α-alumina, for example, from Coors Ceramics in Golden, Colo.

All experiments were performed with deionized water and commercially available $Al_2O_3$ powder, for example, A16-SG from Alcoa Corporation in Bauxite, Ariz. having an equiaxed particle shape, with an average particle size of 0.4 μm, and a specific surface area of 8.5 $m^2$ per gram. Two separate sets of suspensions were prepared: (1) dispersed and (2) flocculated. Dispersed suspensions were prepared by first adding 20 vol. % alumina powder to an aqueous solution of 0.01 M NaCl followed by the dropwise addition of concentrated hydrochloric acid to achieve a pH of 4. Flocculated suspensions were prepared by simply adding 20 vol. % alumina powder to an aqueous solution of 0.01 M NaCl and 0.03 g maltodextrin/g alumina. Commercially-available maltodextrin can be used, for example, Maltrin M040 from Grain Processing Corporation in Muscatine, La. Next, all suspensions were poured into sealed Nalgene bottles and placed on a shaker for 24 hours prior to slip casting.

Suspensions were slip cast onto a flat surface of a plaster mold. Cylindrical pellets were formed by firmly placing a flat sheet of acrylic (5.4 mm thick) onto the plaster mold and then pouring the alumina suspension into an array of circular holes (14.3 mm diameter) previously drilled through the acrylic sheet. Next, the pellets were dried in open air for 24 hours and then sintered, also, in open air. The sintering was performed at temperatures from 1050° C. to a maximum temperature of 1500° C. at increments of 1050° C., 1200° C., 1300° C. and 1500° C. for 3 hours and then cooled to room temperature. In other words, each pellet, of a given specimen type (either dispersed or flocculated) was sintered at maximum temperatures of 1050° C., 1200° C., 1300° C. and 1500° C. Hence, there are 8 pellet samples that are examined, including 2 that are not sintered at all. After cooling, each alumina specimen underwent density measurements, based on the Archimedes principle, using water or mineral oil immersion. Mineral oil is preferred because it avoids disintegration of the green pellets.

Luminescence Spectroscopy

Laser-excited luminescence spectra were obtained using a an argon-ion laser, for example, from Coherent in Santa Clara, Calif., at excitation wavelength of 351.1 nm and 514.5 nm. Emission was measured in both CW and gated modes of detection. For low-temperature spectroscopy (77 and 4.2 K), samples were cooled in a glass cryostat with quartz optical windows. Luminescence was dispersed by a McPherson 2061 1-m focal-length and/or 0.3-m monochromator and detected by Princeton Instruments IRY 1024/G/B intensified photodiode array or CCD camera. For time-resolved detection, a Princeton Instruments FG-100 pulse generator was employed with various detector delay times and gate widths. The luminescence of the component in the ceramic surface was compared to the predetermined reference measurement of luminescence generated from a reference having a known density. A luminescence calibration curve for a given ceramic composition sintered at increasing temperatures was obtained and the luminescence of the ceramic sample compared thereto.

Scanning Mirocracks

Alumina heterogenieties (e.g., microcracks and fractures) created during pellet production were scanned via automated translation of the pellets through the optical plane of a semi-focused Argon ion laser operating in the UV-excitation mode, i.e., $\lambda_{ex}$=351.1 nm. As the alumina pellet translated through the laser's path, the resultant luminescence was collected by a collimating objective, focused into a 0.3-m model 210 McPherson monochromator and detected by a Roper Scientific intensified-charge-coupled-device (CCD). Next, the integrated luminescence intensity was plotted as a function of sample position. The severity of the imperfection was quantified by measuring the relative luminescence intensity from the imperfection versus the background level of intensity.

Imaging

Imaging was performed with a Research Compound Fluorescence Microscope, for example, from Leica Microsystems, Inc. An ozone free xenon high pressure lamp, for example, HB075, was used for excitation with suitable filter sets for excitation. Imaging was performed in two modes: the first was based on natural luminescence of the $Cr^{3+}$ ions present in alumina, while the second mode was based on staining the alumina pellets with a Zyglo 2L-60D fluorescent dye (Magnaflux Corp., Glenville, Ill.). The staining was performed for 3-minutes followed by washing the sample thoroughly with deionized water to remove any non-absorbed dye and dried for subsequent analysis. The following sets of filters were used for fluorescence based microscopy images: first, a UV filter set (excitation interference filter BP 360/40, dichroic mirror at 400 nm and suppression filter LP 425); second, a violet filter set (excitation filter was 420–490, dichroic mirror 510 nm and suppression filter LP 510); and third, a green filter set (excitation filter BP 546–14, dichroic mirror 580 and suppression filter 590).

Results and Discussion

Density Measurements

Results of density measurements via the Archimedes principle are summarized in Table 1 below. Here, it can be seen that the alumina density increased with increasing sintering temperature. Likewise, the nature of the starting suspension (i.e., dispersed or flocculated) affected the density of the samples. For example, the dispersed, green specimens have a higher density than the flocculated green specimens because of the higher electrostatic repulsive forces between particles in the dispersed, slip-casting suspension. In addition, the different sintering temperatures produced a broad range of pellet densities from about 54% to about 97%.

TABLE 1

Summary of Density Calculations

| Sintering Temperature (° C.) | Percent of Theoretical Density* | |
|---|---|---|
| | Dispersed | Flocculated |
| not sintered | 62.7 (±0.1) | 54.0 (±0.8) |
| 1050 | 64.5 (±0.7) | 54.4 (±0.6) |
| 1200 | 71.2 (±1.7) | 62.2 (±1.6) |
| 1300 | 78.6 (±1.7) | 71.9 (±1.4) |
| 1500 | 96.0 (±2.7) | 97.3 (±1.7) |

*Standard deviations indicated in parentheses.

Luminescence Spectra of Alumina

Figure 9:
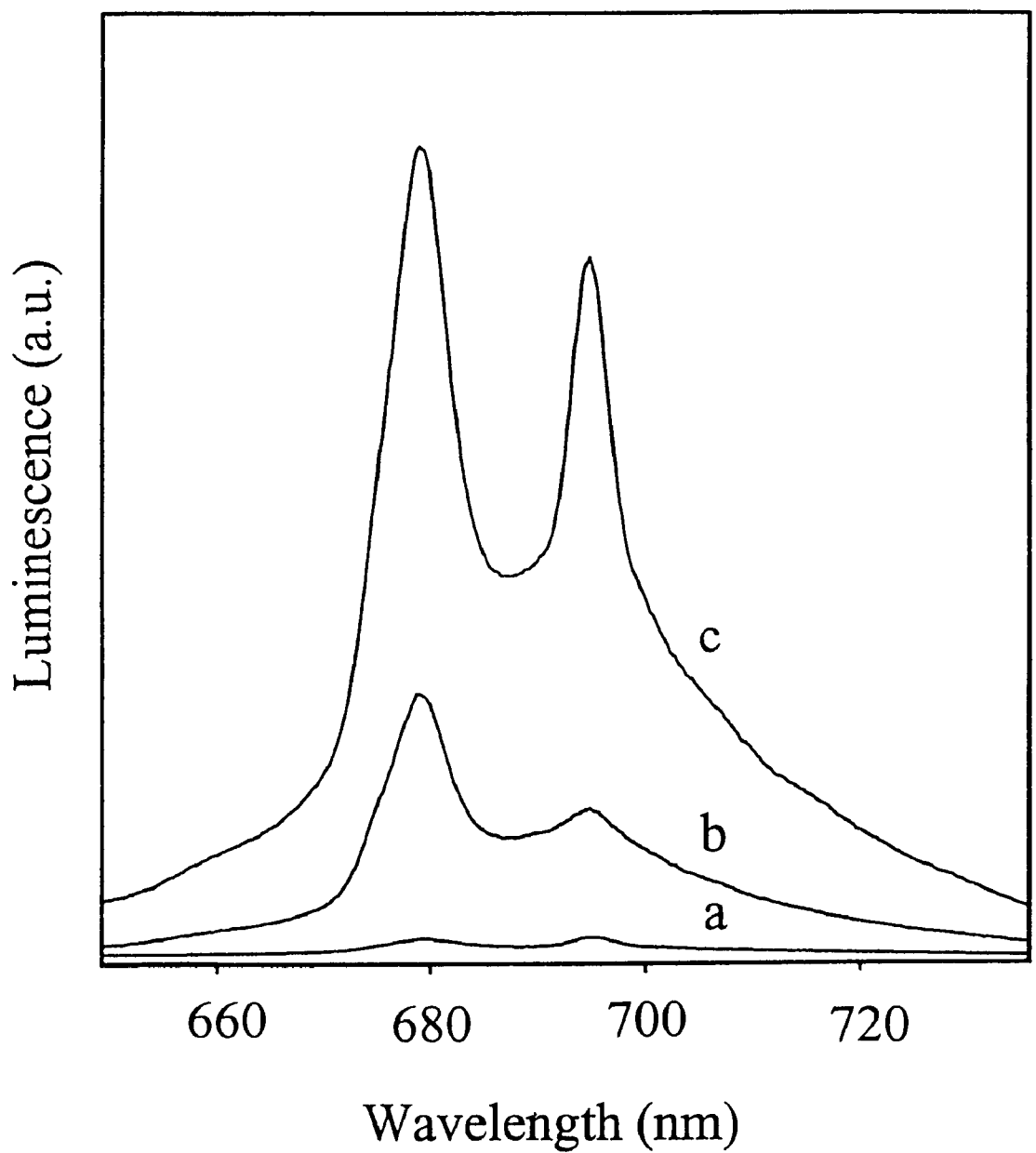
FIG. 9 shows a room temperature fluorescence spectra of three alumina specimens.

FIG. 9 shows a typical room-temperature luminescence spectra of alumina samples excited with an argon-ion laser at 351.1 nm. Spectrum (a) corresponds to a nonsintered (green) sample (density ~62%). Spectras (b) and (c) correspond to samples sintered at 1200° C. (density 71%) and 1500° C. (density 97%), respectively. The size of the laser probe beam was about 10 mm$^2$.

The data in FIG. 9 clearly indicates that luminescence intensity increases with sintering temperature and sample density. Moreover, spectral characteristics indicate that the main luminescence originated from chromium ion ($Cr^{3+}$) impurities naturally present in the aluminas. Thus, because trace amounts of chromium ions are present in most alumina compositions utilized in commercial ceramic applications, exciting the chromium ion to luminescence can advantageously be utilized to determine density and/or density fluctuations of the alumina ceramic because luminescence of chromium ions (typically $Cr^{3+}$) in alumina is related to the density of the alumina ceramic.

The large increase in luminescence from sintered alumina is caused by several factors. One factor is that photon attenuation, resulting from light scattering, decreases in samples with higher densities. In other words, the number of pores acting as scattering centers decreases with increasing sintering temperature. In turn, this increases transmission and/or excitation depth and therefore, the observation of higher luminescence intensity.

Figure 10:
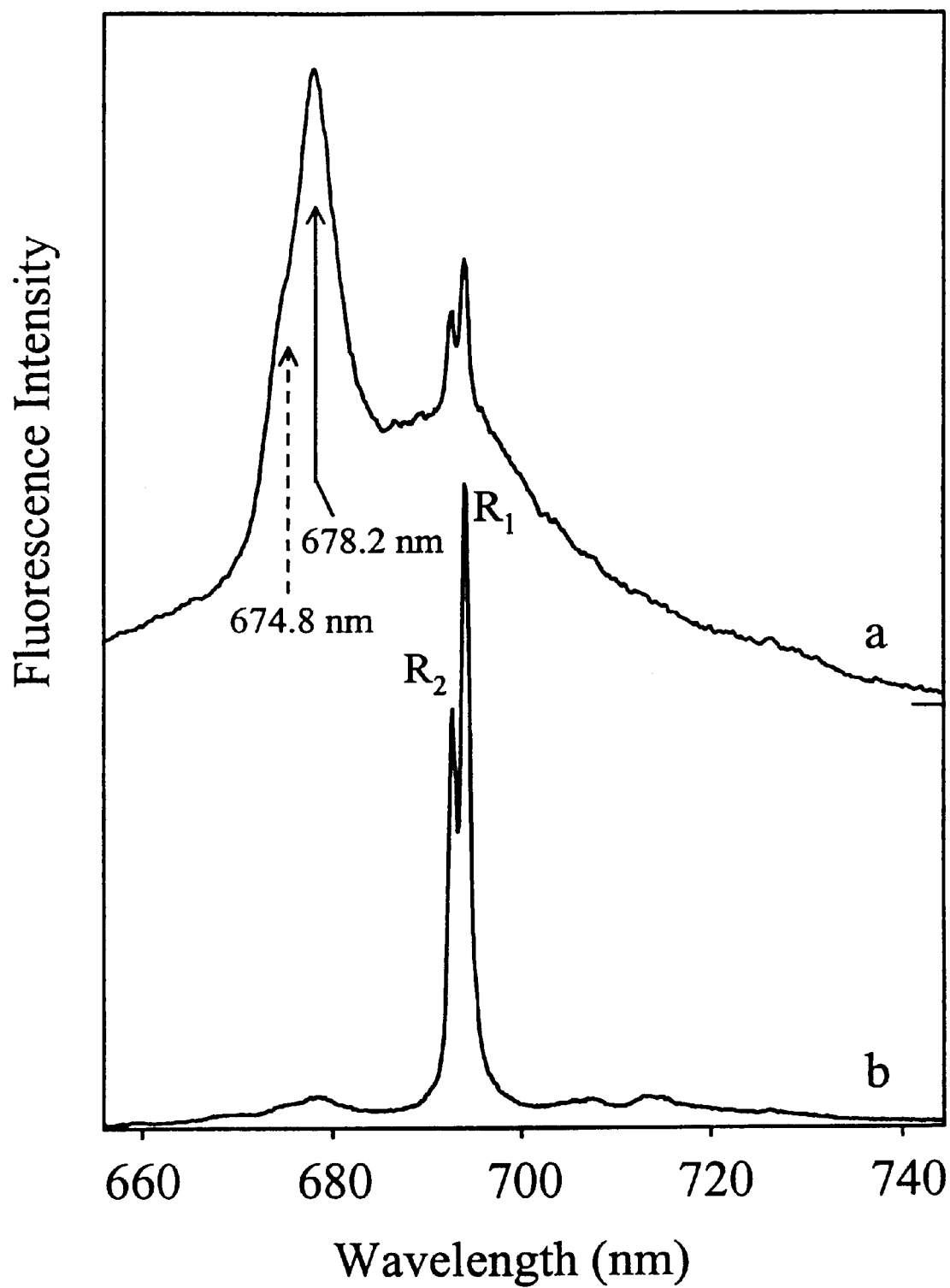
FIG. 10 shows an excitation-dependent spectra for a high-density polycrystalline alumina.

Spectrum (b) in FIG. 10 shows the typical luminescence of a fully-dense specimen of polycrystalline alumina that was obtained from a commercial supplier and excited by a wavelength of 514.5 nm. An identical spectrum was obtained from slip cast alumina specimens that were excited at 514.5 nm after sintering at 1500° C. (data not shown). Spectrum (b) in FIG. 10, in agreement with literature data, reveals only the standard R-line (~693 nm) luminescence of $Cr^{3+}$ ions in perfect octahedral environment. In contrast, UV excitation by a wavelength of 351.1 nm (spectrum (a)) shows a much stronger luminescence at ~678 nm.

The band observed at 678.2 nm (solid arrow) and its shoulder at 674.8 nm in FIG. 10 correspond to $Cr^{3+}$ ions in different sites, i.e., Cr ions in lower symmetry sites (a contribution from grain boundary sites cannot be excluded). Such lower symmetry sites could arise from anisotropic electron repulsion energies within slightly larger volumes of the quasi-octahedra in which some of the $Cr^{3+}$ ions reside, although tetragonal crystal symmetry distortion is possible. The band at ~678 nm in curve (a) of FIG. 10 (solid arrow) is approximately 25% narrower than the same band in curve (c) of FIG. 9, indicating that this particular sample has a smaller distribution of local stresses, i.e., a smaller stress gradient across the alumina specimen. This indicates that not only the luminescence intensity, but also the spectral "fingerprint", as shown in FIGS. 9 and 10, are useful in a manufacturing setting.

Figure 11:
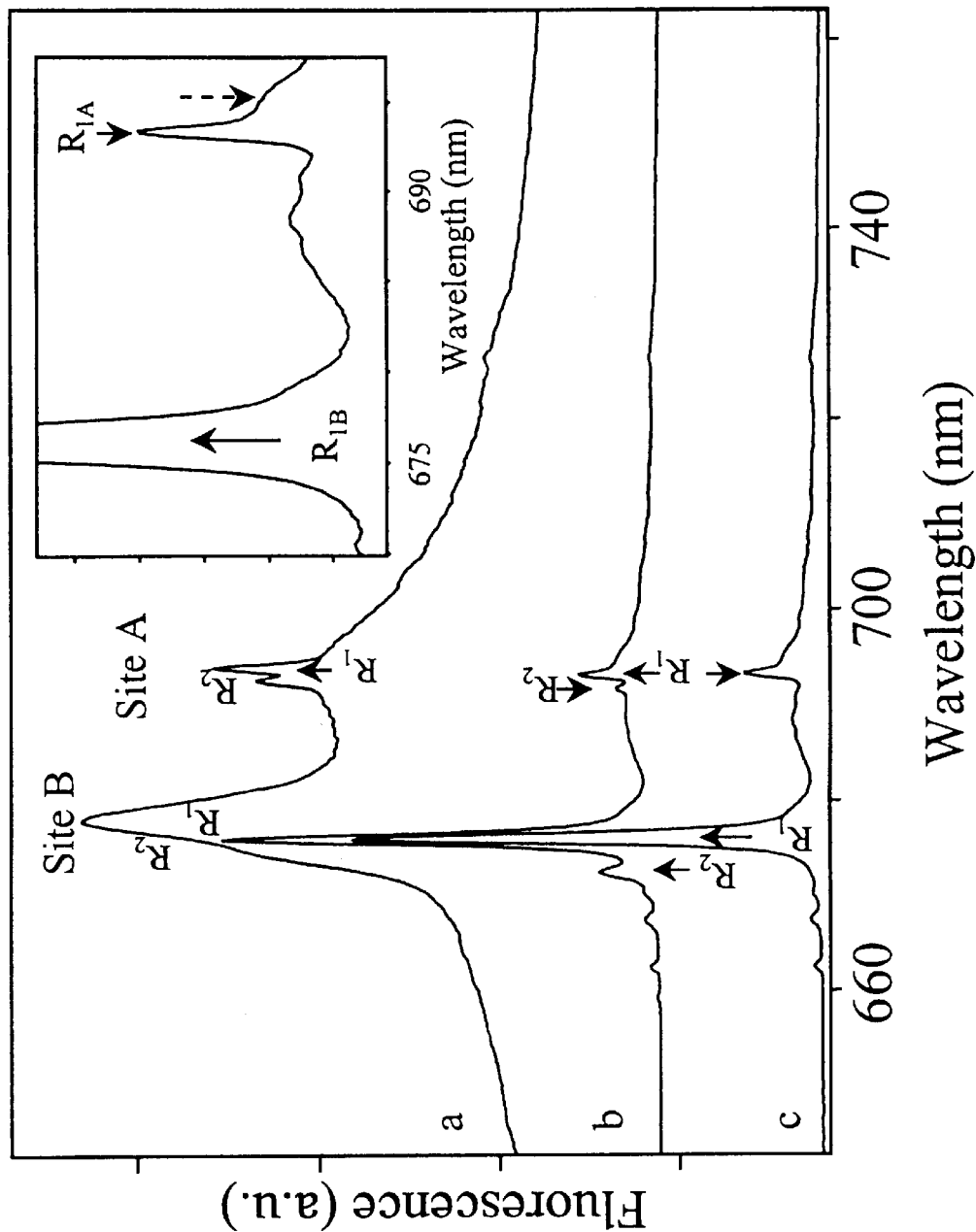
FIG. 11 shows the temperature dependence of chromium-impurity fluorescence of a high-density polycrystalline alumina.

Additionally, due to the partly disordered nature of alumina ceramics, spectral broadening effects and emissions from different sites were observed. This is illustrated in FIG. 11, which shows spectra a–c obtained at 300, 77, and 4.2 K, respectively, with an excitation wavelength of 351.1 nm. The purpose of the measurements at 4.2 and 77 K was to minimize thermal broadening. The spectra are normalized so that the intensities of the most intense feature in each spectrum are equal. As discussed above, these spectra suggest that $Cr^{3+}$ ions occupy different sites labeled as A and B.

When $Cr^{3+}$ ions are irradiated at 351.1 nm, high-energy bands are excited, and some of the energy is lost through non-radiative transitions to the $^2E$ state(s) as described in FIG. 2. The $^2E$ state decays by spontaneously emitting a doublet, the components of which are assigned as $R_i$ (i=1, 2) lines. Thus, $Cr^{3+}$ impurity ions in both sites (A & B) fluoresce via vibronically structured $^2E \rightarrow ^4A_2$ transitions. Spectrum (a) in FIG. 11 shows that fluorescence (T=300 K) from B sites is broader than that from A sites. The much larger inhomogeneous broadening observed for B sites is most probably caused by more random crystal field distortion at each chromium ion.

Visual Assessment of Density by Color

UV-excited luminescence in the "red" wavelength region (~600–750 nm) increases with alumina density in relation to emission observed in the "blue/green" (380–500 nm) wavelength region. Thus various luminescence signals lead to distinguishable hues of laser-excited aluminas sintered at different temperatures as a visual assessment of alumina density based on color.

For example, images of four alumina pellets, excited with an argon-ion laser at 351.1 nm and obtained from the same starting material but different final density, are shown in FIG. 12. Frame A shows luminescence from the non-sintered green body preparation, while frames B, C and D correspond to aluminas sintered at 1200° C., 1300° C., and 1500° C., respectively. The "green body" image was obtained with an exposure time 2.5 times longer than the images in frames B–D. The densities of the aluminas in frames A, B, C, and D are 62%, 71%, 77%, and 97%, respectively, as established by Archimedes density measurements. Clearly, color changes with density, i.e., the low-density, green body preparation exhibits mainly a blue luminescence with progressively additive red luminescence as density increases. Thus, a variety of microscopic conditions in alumina ceramics due to the low-, medium-, and high-field surroundings of the $Cr^{3+}$ ions, can produce a broad range of colors as shown in FIG. 5. A fluorescing dye was not used in any of the specimens shown in FIG. 5.

Density Calibration Curve

FIG. 3, as discussed previously, shows a calibration curve of luminescence as a function of density. These results show that increases in alumina density are accompanied by increases in the (UV-excited) integrated luminescence intensity in the red region (600–750 nm). As shown in FIG. 3, similar results were obtained from two sets of samples made under dispersed and flocculated conditions. A fluorescing dye was not used in any of the specimens shown in FIG. 3.

Also shown in FIG. 3, both the dispersed and flocculated specimens exhibited a dramatic "jump" in luminescence intensity after partially sintering the green bodies at 1050° C. The change in alumina density is negligible before and after partial sintering the dispersed and flocculated specimens. The sudden jump in luminescence intensity is likely associated with a diminished spatial frequency of scattering centers (pores). Also, sintering shrinkage may increase the relative contribution of the piezoelectric effect. Hence, to determine whether the ceramic sample is of a particular, desirable density, the manufacturer will simply illuminate (excite) the ceramic sample and determine whether the intensity of the luminescence is that of a ceramic with a particular density, by correlating the luminescence on the calibration curve with that of its corresponding density measurement.

Scanning Microcracks and/or Density Gradients

Scanning a semi-focused laser beam across polycrystalline alumina reveals an increase of luminescence intensity whenever the beam encounters microcracks. When the laser probes a smooth portion of the specimen surface, only background luminescence is observed. However, when an imperfection such as a crack is brought into the path of the laser, luminescence increases because of a larger cross-section of the ceramic being exposed to the laser light and/or tighter focus of the laser beam within the microcrack. Furthermore, quantifying the severity of the cracks was achieved by measuring the relative luminescence intensity observed by the detector. A ceramic specimen (partially sintered) was scanned in the forward direction (+X) followed by scanning the same distance in the reverse direction (−X) as shown in FIG. 4. A major increase in luminescence intensity was observed as the laser probed a large crack. This is the result of the laser probing a greater surface area. Similarly, minor increases in luminescence intensity (observed as small spikes in FIG. 4) are the result of less blatant imperfections in the highly-sintered alumina. Furthermore, with an increase in scanning resolution (i.e., a proper translation stage), a more detailed profile of the surface microcracks was obtained. A resolution of several $\mu$m was used. Thus scanning could have significant potential in nondestructive evaluation of cracks/fractures and other production-caused heterogeneities in ceramic processing.

Imaging Flaws in Ceramics

Microcracks and density gradients were also revealed via luminescence-based microscopy. FIG. 5 shows two examples of flaw imaging. Frame A is an image of the inherent luminescence of a sintered alumina specimen without a fluorescent staining dye. Frame B shows the same region of the same alumina specimen as imaged with the fluorescent staining dye. The same (predominant) microcrack stretches diagonally across each image. Additionally, density gradients are easily distinguishable as light and dark regions on the image in Frame B of FIG. 5.

FIG. 6 illustrates another example of the use of this method to image cracks and density gradients in sintered alumina. Both images in FIG. 6 were obtained from the same, sintered alumina specimen that was stained with fluorescent dye and imaged with a violet filter. Frame A reveals distinct gradients in luminescent color arising from density gradients in the alumina specimen. Dark areas correspond to high density regions and the bright areas to low density regions. In image B, the violet excitation of the dye clearly shows that microcracks are associated with low density regions where porosity is the greatest (bright regions in the image).

Chemiluminescence Based Detection of Ceramic Flaws

FIGS. 7 and 8 show a plug shaped alumina sample with cracks and/or density gradients obtained with a chemiluminescent kit (containing a fluorescent dye, oxalate, and hydrogen peroxide) combined with solution of a chemiluminescence initiator (salicylate catalyst) and a ceramic penetrant. The alumina in FIG. 7 was stained with the chemiluminescent mixture and after 2–5 minutes the excess of the chemiluminescent solution agent was wiped from the alumina surface. Here, no external excitation was used to generate these images. FIG. 7 reveals cracks, while FIG. 8 shows an image of a density gradient inside the alumina sample. In contrast, luminescence-based imaging discussed above (using UV-laser excitation), is more suitable for detection of cracks and density gradient on (or close) to the alumina surface. This is due to the inaccessibility of the bulk of material to UV excitation.

It is to be understood that the above description is intended to be illustrative, and not restrictive. Various modifications and alterations of this invention will become apparent to those skilled in the art from the foregoing description without departing from the scope and the spirit of this invention, and it should be understood that this invention is not to be unduly limited to the illustrative embodiments set forth herein. Accordingly, the invention is not to be considered as limited by the foregoing description but is only limited by the scope of the appended claims.

REFERENCES

1. T. Abraham, "Advanced Ceramic Powder and Nano-Sized Ceramic Powder: An Industry and Market Overview," in *Ceramic Transactions Volume 62, Science, Technology, and Commercialization of Powder Synthesis and Shape Forming Processes*, edited by J. J. Kingsley, C. H. Schilling, and J. H. Adair (American Ceramic Society, Westerville, Ohio, U.S.A., 1996), pp. 3–14.

2. D. Segal, "Chemical Preparation of Powders," in *Materials Science in Technology, Volume 17A, Processing of Ceramics, Part 1*, edited by R. J. Brook, R. W. Cahn, P. Haasen, and I. J. Kramer (VCH Verlagsgesellschaft mbH, Weinheim, Federal Republic of Germany, 1996), pp. 70–98.

3. D. Segal, "Chemical Synthesis of Advanced Ceramic Materials" (Cambridge University Press, Cambridge 1989).

4. F. F. Lange, "Powder Processing Science and Technology for Increased Reliability," *J. Am. Ceram. Soc.* 72 [1]3–15 (1989).

5. F. F. Lange, "Sinterability of Agglomerated Particles," *J Am. Ceram. Soc.* 67 [2]83–89 (1984).

6. Schilling, C. H., and Gray, J. N., "Needs and Opportunities for NDE in Ceramic Processing," in *Ceramic Transactions, Volume 67: Nondestructive Evaluation of Ceramics*, C. H. Schilling and J. N. Gray, editors, American Ceramic Society, Westerville, Ohio, 1998, pp. 1–19.

7. C. H. Schilling, V. J. Garcia, R. M. Smith, and R. A. Roberts, "Ultrasonic and Mechanical Behavior of Green and Partially Sintered Alumina: Effects of Slurry Consolidation Chemistry," *J. Am. Ceram. Soc.* 81 [10]2629–2639 (1998).

8. V. J. Garcia, C. H. Schilling, S. P. Huss, J. N. Gray, M. Sikora, P. Tomasik, and C. P. Li, "X-ray NDE of Density Gradients During Alumina Powder Consolidation: Effects of Suspension Chemistry," in *Advances in Process Measurements for the Ceramic Industry*, edited by A. Jillavenkatesa and G. Y. Onoda (American Ceramic Society, Westerville, Ohio, 1999), pp. 307–322.

9. C. H. Schilling, V. J. Garcia, R. M. Smith, and R. A. Roberts, "Ultrasonic and Mechanical Behavior of Green and Partially Sintered Alumina," *J. Am. Ceram. Soc.* 81 (10) 2629–39 (1998).

10. R. A. Roberts, "A Dry-Contact Coupling Technique for Ultrasonic Nondestructive Evaluation of Green-State Ceramics", *Mater. Eval.* 46[May] 758–66, (1988).

What is claimed as new and desired to be protected by Letters Patent of the United States is:

1. A nondestructive method for determining density of a ceramic body comprising:

exposing a surface of said ceramic to an input energy so as to excite a component from the surface of said ceramic;

obtaining a measurement of an emitted energy from said excited component; and comparing said measurement with a predetermined density reference so as to obtain a density for said ceramic body.

2. The method of claim 1 wherein said component is a metal cation.

3. The method of claim 1 wherein said component comprises a chromium ion.

4. The method of claim 1 wherein said component is at least one member selected from the group consisting of transition metal ions.

5. The method of claim 1 wherein said ceramic comprises alumina.

6. The method of claim 1 wherein said ceramic is a sintered ceramic.

7. The method of claim 1 wherein said input energy has a wavelength between about 300 nm to about 650 nm.

8. The method of claim 1 wherein said input energy has a wavelength about 500 to about 650 nm.

9. The method of claim 1 wherein said emitted energy has a wavelength between about 650 nm to about 850 nm.

10. The method of claim 1 wherein said density is determined to detect ceramic surface imperfections.

11. The method of claim 1 wherein said density is determined without damaging said ceramic.

12. The method of claim 1 wherein said reference is a series of measurements of test emitted energy attained over a defined range of ceramic density values.

13. The method of claim 1 wherein said measurement is performed by luminescence based microscopy.

14. The method of claim 1 wherein said measurement is performed by fluorescence based microscopy.

15. The method of claim 1 wherein said ceramic is stained with a dye.

16. The method of claim 1 wherein said ceramic is a green ceramic.

* * * * *